United States Patent [19]

Matsuzaki

[11] Patent Number: 4,489,693
[45] Date of Patent: Dec. 25, 1984

[54] AIR-FUEL RATIO CONTROL SYSTEM
[75] Inventor: Takeshi Matsuzaki, Mitakashi, Japan
[73] Assignee: Fuji Jukogyo Kabushiki Kaisha, Tokyo, Japan
[21] Appl. No.: 550,078
[22] Filed: Nov. 9, 1983
[30] Foreign Application Priority Data
Nov. 10, 1982 [JP] Japan .................................. 57-197953
[51] Int. Cl.³ .............................................. F02M 7/00
[52] U.S. Cl. ................................................... 123/440
[58] Field of Search ........................ 123/440, 489, 492

[56] References Cited
U.S. PATENT DOCUMENTS

| 4,103,657 | 8/1978 | Minami | 123/440 |
| 4,132,199 | 1/1979 | Kuroiwa et al. | 123/440 |
| 4,202,295 | 5/1980 | Kondo et al. | 123/492 |
| 4,364,358 | 12/1982 | Shikata et al. | 123/440 |
| 4,385,608 | 5/1983 | Ohgami et al. | 123/440 |
| 4,398,517 | 8/1983 | Kubota et al. | 123/440 |

Primary Examiner—Tony M. Argenbright
Attorney, Agent, or Firm—Martin A. Farber

[57] ABSTRACT

A system for controlling the air-fuel ratio of an air-fuel mixture for an internal combustion engine having a two-barrel carburetor. The system is provided with an O₂ sensor for detecting the concentration of oxygen in the exhaust gases, an on-off electromagnetic valve for correcting the air-fuel ratio of the air-fuel mixture supplied by the carburetor and an electronic control circuit. The electronic control circuit operates to compare output signals of the detector with a stoichiometric value, and to produce driving pulses for driving the on-off electromagnetic valve and for controlling the air-fuel ratio to a value approximately equal to the stoichiometric air-fuel ratio. A fixed signal generating circuit is selectively connected to the electronic control circuit. The two-barrel carburetor has an actuator actuated by the vacuum at the venturi of the carburetor for opening a throttle valve of the secondary side of the carburetor. A first vacuum switch is provided to be operated in response to the vacuum in the intake passage and a second vacuum switch is provided to be operated by the vacuum in the secondary side of the carburetor. When one of vacuum switches is operated, the fixed signal generating circuit is connected to the electronic control circuit for providing a fixed duty ratio for the valve and renders the electronic control circuit non-responsive to the output of the O₂ sensor.

3 Claims, 4 Drawing Figures

AIR-FUEL RATIO CONTROL SYSTEM

BACKGROUND OF THE INVENTION

The present invention relates to an air-fuel ratio control system with an electrically-controlled carburetor in an intake system of an internal combustion engine and with a three-way catalytic converter in an exhaust system. The air-fuel ratio control system controls the air-fuel ratio of an air-fuel mixture to a stoichiometric air-fuel ratio at which the three-way converter operates most effectively and controls the air-fuel ratio to a fixed rich air-fuel ratio (small air-fuel ratio) at heavy load driving in the entire range of engine speed, so that the controlled air-fuel ratio range and the fixed air-fuel ratio range are adjusted properly to vehicle driving conditions.

A conventional air-fuel control system is provided with a detecting device for detecting heavy load operation of the engine and a control circuit for controlling the air-fuel ratio to a fixed rich ratio in order to produce high power for the heavy load operation.

In such a system, because the intake passage vacuum and throttle opening degree vary in dependency on the load, a certain value of the intake passage vacuum or throttle opening degree is selected for the detection of heavy load operation. For instance, in the load characteristic shown in FIG. 1, a curve A is the torque curve at full throttle and curve B shows one of torque-engine speed characteristics of a vacuum detecting device. Using the intake passage vacuum detecting method, in the range beneath the curve B, the air-fuel ratio is controlled to the stoichiometric air-fuel ratio for partial power operation, but in the range above the curve B the ratio is fixed to a rich air-fuel ratio for high power operation. Also in the throttle opening degree method, ranges for two operations are defined by a curve C.

As clearly shown in FIG. 1, the fixed air-fuel ratio range above the curve B is wide in the low and middle engine speed zone and is narrow in the high speed zone. It is unfavourable for high speed driving under heavy load conditions, that the fixed rich air-fuel ratio range is narrow in a high speed zone.

On the other hand, using the throttle opening degree detecting method the fixed air-fuel ratio range at low speed zone is narrower than using the vacuum detecting method, but the exhaust gas purification effect is still not sufficient. Further, the fixed air-fuel ratio range at middle and high speed zone is broad, resulting in increases of noxious gas emission.

SUMMARY OF THE INVENTION

In order to overcome such defects of conventional systems, the present invention seeks to provide an air-fuel ratio control system for an internal combustion engine, which improves the high power range at a rich air-fuel ratio, so that a wide high power range may be obtained in an entire speed range of an engine.

According to the present invention, there is provided an air-fuel ratio control system for a carburetor of an internal combustion engine having an intake passage, two venturis in a primary side and secondary side of said carburetor, two throttle valves in said primary and secondary sides, an exhaust passage, an O₂ sensor for detecting the concentration of the constituent of exhaust gases passing through said exhaust passage, an on-off electromagnetic valve for correcting the air-fuel ratio of the air-fuel mixture supplied by an air-fuel mixture supply means, an electronic control circuit comprising a comparator for comparing an output signal of said O₂ sensor, an integrating circuit and a driving circuit for producing driving pulses for driving said electromagnetic valve in dependency on an output signal of said integrating circuit for controlling the air-fuel ratio to a value approximate to the stoichiometric air-fuel ratio, the improvement comprising a vacuum operated actuator responsive to the vacuum at the venturis as an indication of the condition of operation of the internal combustion engine; a fixed signal generating circuit for supplying a rich air-fuel ratio signal to the driving circuit; and switch means adapted to be operated by vacuums in said secondary side and said intake passage so as to render the output signal of the O₂ sensor ineffective when the levels of vacuums are above predetermined levels and to supply the fixed signal to the driving circuit.

The present invention will be more apparent from the following description made with reference to the accompanying drawings of the preferred embodiment.

DETAILED DESCRIPTION OF THE PREFERRED EMBODIMENT

Figure 2:
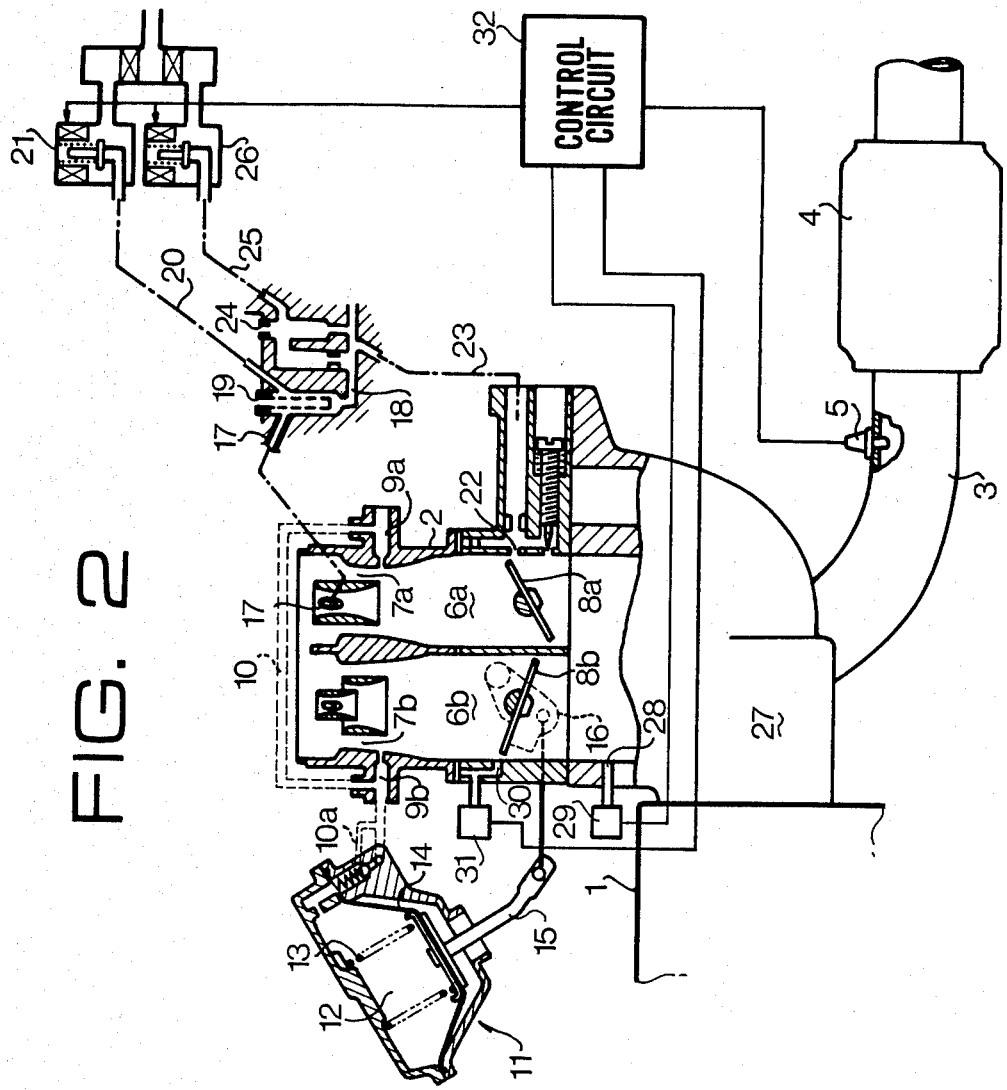
FIG. 2 shows the construction of an air-fuel control system in accordance with the present invention.

In FIG. 2, numeral 1 designated an internal combustion engine which is provided with a two-barrel carburetor 2 comprising a primary side and a secondary side, and an exhaust pipe 3. A catalytic converter 4 with three-way catalyst is disposed in the exhaust pipe 3 and and O₂ sensor 5 is also disposed in the exhaust pipe 3 at upstream side of the catalytic converter 4 for detecting the oxygen concentration of exhaust gases.

The carburetor 2 is provided with a primary side passage 6a and a secondary side passage 6b, venturis 7a, 7b and throttle valves 8a, 8b. In narrow portions of venturis 7a and 7b, vacuum ports 9a and 9b are disposed. Both ports are communicated with a vacuum chamber 12 of a vacuum operated actuator 11 of diaphragm type through a vacuum passage 10. The actuator comprises a diaphragm spring 13, a diaphragm 14, the vacuum chamber 12, and a link mechanism 15 connected to a lever 16 of the throttle valve 8b in the secondary side. A main nozzle 17 opening to the venturi 7a of the primary side communicates with a main fuel passage 18 which is provided with an air bleed 19. The air bleed 19 is communicated with an on-off type electromagnetic valve 21 through an air correcting passage 20 for supplying air to the air bleed 19. Branching off from the passage 18, a slow fuel passage 23 communicates to a slow port 22 opening in vicinity of the closed position of the throttle valve 8a. A slow air bleed 24 is communicated with an on-off type electromagnetic valve 26 through an air correcting passage 25. On the other hand, although the venturi 7b of the secondary side is provided with a main fuel system, an air correcting system such as that of the primary side is not provided because it is not necessary to control the air-fuel ratio during high power operation by the operation of the secondary side of the carburetor. If the air-fuel ratio control is required in high power operation, the electromagnetic valve 26 can be used for the control function, since the electromagnetic valve 26 for light load operation is not used for such high power operation.

In this embodiment of the present invention, a port 28 is formed in an intake pipe 27 and a vacuum switch 29 is provided to be communicated with the intake pipe through the port 28. The vacuum switch 29 is adapted to be turned on when the vacuum is higher than a predetermined value. Further, a port 30 is formed to be communicated with the secondary side passage 6b. The port 30 is located at a position at upstream side of the closed throttle valve 8b and at a position at downstream side of the throttle valve 8b when the throttle valve 8b is opened beyond a predetermined degree. A vacuum switch 31 is provided at the port 30 so as to be on when the vacuum is higher than a predetermined value.

Figure 1:
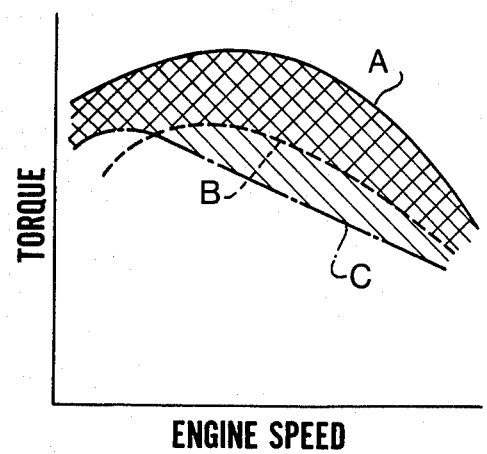
FIG. 1 is a graph showing the ranges of fixed air-fuel ratio in a conventional control system.
Figure 4:
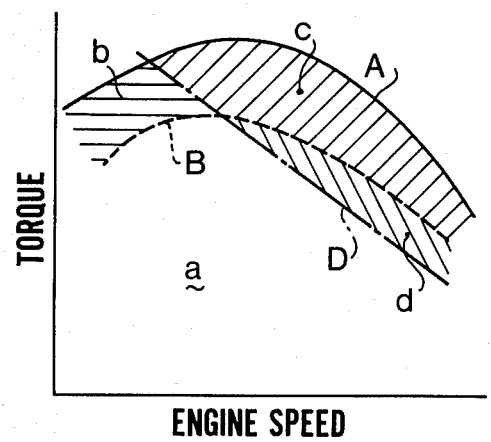
FIG. 4 is a graph showing a range of fixed air-fuel ratio by the system in accordance with the present invention.

Torque-engine speed characteristic of the vacuum switch 29 is selected to have a line B in FIG. 4 and that of the vacuum switch 31 is selected as line D. The line B is the same as the line B of FIG. 1.

The outputs of the $O_2$ sensor 5 and switches 29 and 31 are connected electrically to the electromagnetic valves 21 and 26 through a control circuit 32.

Figure 3:
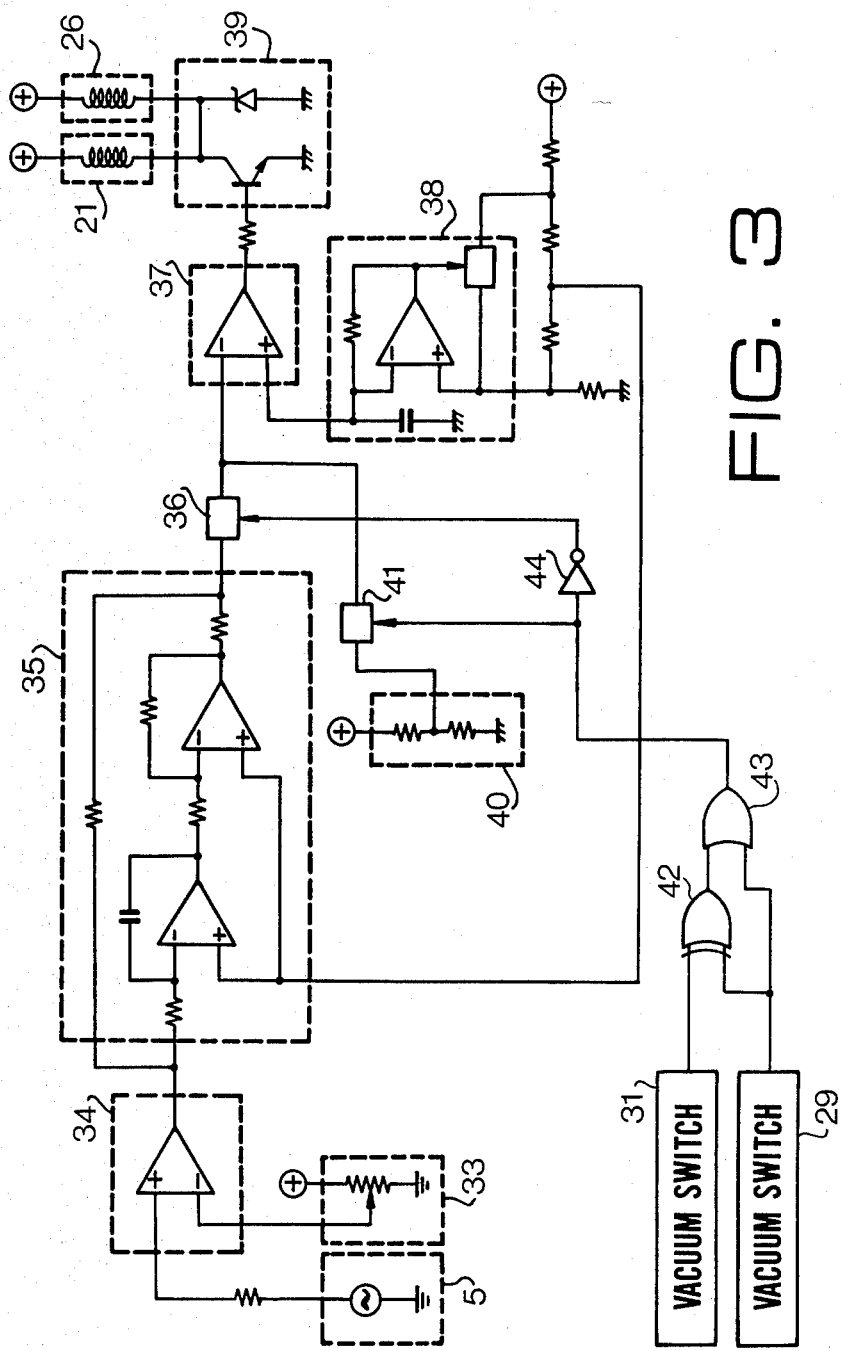
FIG. 3 is a control circuit employed in the system of FIG. 2.

Referring to FIG. 3 showing a control circuit employed in the system, the output signal of the $O_2$ sensor 5 is fed to a comparator 34. The comparator 34 operates to compare the input signal with a reference value applied from a reference value circuit 33 to produce a deviation signal. The deviation signal is fed to a proportional and integrating circuit 35, so that the deviation signal is converted into a proportional and integrating signal. The proportional and integrating signal is fed to a comparator 37 through a semiconductor switch 36 and is compared with triangular pulses fed from a triangular wave pulse generator 38, so that square wave pulses are produced. The square wave pulses are fed to a driver 39 and further to both of the on-off type electromagnetic valves 21 and 26.

In this embodiment of the present invention, a fixed duty ratio signal generating circuit 40 is connected to the comparator 37 through a semiconductor switch 41.

On the other hand, outputs of vacuum switches 29 and 31 are connected with inputs of an EXCLUSIVE-OR gate 42 and outputs of the gate 42 and vacuum switch 29 are connected with inputs of an OR gate 43. Output of the OR gate 43 is connected with a control gate of the switch 36 through an inverter 44 and with a control gate of the switch 41.

At a light load operation and low engine speed, the vacuum at the primary side port 9a is decreased by the atmospheric pressure at the secondary side 6b, so that the actuator 11 does not operate and the throttle valve 8b is closed. Such a light load operation is in a range a below lines B and D in FIG. 4, and the vacuum switches 29 and 31 are off.

To explain the operation of the system in more detail: in the low speed zone or middle or high speed zone at light load, the venturi vacuum obtained at the vacuum port 9a is low and cancelled out by the atmospheric pressure at the port 9b. Therefore, the vacuum in the vacuum chamber 12 of the actuator 11 is almost zero, so that the diaphragm 14 and the link mechanism 15 are engaged by the spring 14 so as to close the secondary throttle valve 8b. At such a time vacuum switches 29 and 31 are turned off. Accordingly outputs of EXCLUSIVE-OR gate 42 and OR gate 43 are at low levels. Therefore, the output of the inverter 44 is high, so that the switch 36 is closed and the switch 41 is opened. Thus, the proportional and integrating circuit 35 is connected to the comparator 37. In such a condition, when exhaust gases having a small oxygen concentration are detected by the $O_2$ sensor 5, the proportional and integrating circuit 35 produces an output signal for correcting the deviation of the air-fuel ratio. According to the output signal, the driver 39 produces output pulses having a greater pulse duty ratio, whereby the opening times of the on-off type electromagnetic valves 21 and 26 increase and as a result, the amount of air passing through passages 20 and 25 increases. Thus, the air-fuel ratio of the mixture fed from the carburetor 2 is increased. When a lean air-fuel ratio is detected, driving pulses having a small pulse duty ratio are produced, whereby the air-fuel ratio is decreased to enrich the mixture fed from the primary side of the carburetor.

When the engine speed increases and the venturi vacuum increases at heavy load, the opening of the primary throttle valve 8a is increased to a heavy load position. The venturi vacuum at the vacuum port 9a is rapidly increased, and accordingly, the vacuum in the vacuum chamber 12 is elevated because of the vacuum introduced therein through the passage 10a, whereby the diaphragm 14 is deflected to open the secondary throttle valve 8b. Accordingly, venturi vacuum is obtained also at the vacuum port 9b and combined with the vacuum at the vacuum port 9a, resulting in a rapid increase in the degree of opening of the secondary throttle valve 8b. Thus fuel is supplied to the secondary side 6b to increase the power. In the power ranges b and c (FIG. 4), the vacuum switch 29 is closed, so that output of OR gate 43 goes to a high level and the switch 36 is opened and the switch 41 is closed. Therefore, a fixed duty ratio signal for a rich air-fuel mixture is fed from the circuit 40 to the comparator 37 through the switch 41. Further, at middle and high speed of the engine, when the throttle valve 8b is widely opened, the vacuum switch 29 is off. However, the vacuum switch 31 is on in the range d of FIG. 4, since the port 30 is located downstream of the throttle valve 8b. Thus, output of EXCLUSIVE-OR gate 42 goes to a high level. Therefore, the air-fuel ratio is fixed to a low value in the same manner as described above.

As described above, in an arrangement according to the present invention, in comparison with the conventional intake passage vacuum method and throttle opening degree method, a wide power range at a fixed air-fuel ratio is obtained in the entire engine speed zone, and the driveability and acceleration is improved.

While the presently preferred embodiment of the present invention has been shown and described, it is to be understood that the this disclosure is for the purpose of illustration and that various changes and modifications may be made without departing from the spirit and scope of the invention as set forth in the appended claims.

What is claimed is:

1. In an air-fuel ratio control system for a two-barrel carburetor of an internal combustion engine having an intake passage, two venturis in a primary side and secondary side of said carburetor, two throttle valves in said primary and secondary sides, an exhaust passage, an $O_2$ sensor for detecting the concentration of the constituent of exhaust gases passing through said exhaust passage, an on-off electromagnetic valve for correcting the air-fuel ratio of the air-fuel mixture supplied by an air-fuel mixture supply means, an electronic control circuit comprising a comparator for comparing an output signal of said $O_2$ sensor, an integrating circuit and a driving circuit for producing driving pulses for driving said electromagnetic valve in dependency on an output signal of said integrating circuit for controlling the air-fuel ratio to a value approximate to the stoichiometric air-fuel ratio, wherein the improvement comprises a vacuum operated actuator responsive to the vacuum at the venturis as an indication of the condition of operation of the internal combustion engine; a fixed signal generating circuit for supplying a rich air-fuel ratio signal to the driving circuit; and switch means adapted to be operated by vacuums in said secondary side and said intake passage so as to render the output signal of the $O_2$ sensor ineffective when the levels of vacuum are above predetermined levels and to supply the fixed signal to the driving circuit.

2. An air-fuel ratio control system according to claim 1 wherein said vacuum operated actuator has a diaphragm defining a vacuum chamber, communicated with venturis of the carburetor so as to be actuated by the vacuum in the carburetor to open the throttle valve in the secondary side.

3. An air-fuel ratio control system according to claim 1 wherein said switch means comprises a first vacuum switch operated by the vacuum in said intake passage, and a second vacuum switch operated by the vacuum in said secondary side of the carburetor at a position adjacent the throttle valve.

* * * * *